United States Patent
Saadat

(10) Patent No.: US 6,855,153 B2
(45) Date of Patent: Feb. 15, 2005

(54) EMBOLIC BALLOON

(76) Inventor: Vahid Saadat, 12679 Kane Dr., Saratoga, CA (US) 95070

( * ) Notice: Subject to any disclaimer, the term of this patent is extended or adjusted under 35 U.S.C. 154(b) by 96 days.

(21) Appl. No.: 09/846,876

(22) Filed: May 1, 2001

(65) Prior Publication Data

US 2002/0165572 A1 Nov. 7, 2002

(51) Int. Cl.⁷ .............................................. A61M 29/02
(52) U.S. Cl. ..................................................... 606/194
(58) Field of Search .................... 606/194, 198, 606/191, 195, 158

(56) References Cited

U.S. PATENT DOCUMENTS

| | | | |
|---|---|---|---|
| 4,638,803 A | * | 1/1987 | Rand ............................ 604/175 |
| 4,710,192 A | | 12/1987 | Liotta et al. |
| 4,819,637 A | | 4/1989 | Dormandy, Jr. et al. |
| 5,423,829 A | | 6/1995 | Pham et al. |
| 5,456,666 A | | 10/1995 | Campbell et al. |
| 5,458,572 A | | 10/1995 | Campbell et al. |
| 5,749,883 A | * | 5/1998 | Halpern ....................... 600/114 |
| 5,766,203 A | | 6/1998 | Imran et al. |
| 5,843,163 A | | 12/1998 | Wall |
| 5,925,060 A | * | 7/1999 | Forber ......................... 606/191 |
| 5,928,260 A | * | 7/1999 | Chin et al. ................... 604/107 |
| 6,036,689 A | | 3/2000 | Tu et al. |
| 6,120,534 A | | 9/2000 | Ruiz |
| 6,162,245 A | | 12/2000 | Jayaraman |
| 6,179,867 B1 | | 1/2001 | Cox |
| 6,187,034 B1 | | 2/2001 | Frantzen |
| 6,346,117 B1 | * | 2/2002 | Greenhalgh .................. 606/200 |
| 6,350,270 B1 | * | 2/2002 | Roue ........................... 606/151 |
| 6,356,782 B1 | * | 3/2002 | Sirimanne et al. .......... 128/899 |

FOREIGN PATENT DOCUMENTS

| | | | |
|---|---|---|---|
| WO | WO 97/26939 | * | 7/1997 |
| WO | WO 99/03404 | | 1/1999 |
| WO | WO 00/27292 | | 5/2000 |
| WO | WO 00/72909 | | 12/2000 |
| WO | WO 01/12104 | | 2/2001 |
| WO | WO 01/15608 | | 3/2001 |

* cited by examiner

Primary Examiner—Ismael Izaguirre

(57) ABSTRACT

An embolic balloon assembly is disclosed herein. The assembly includes a detachable balloon system which expands while aspirating a quantity of surrounding blood to occlude a vessel or aneurysm. The balloon has a distensible membrane having a plurality of orifices throughout its surface. Within the distensible membrane is a plurality of expandable members made from a shape memory alloy, e.g., Ni—Ti alloy, which expand upon application of a stimulus. Alternatively, the expandable members or a single expandable wire may be inserted separately into the distensible membrane. Once the balloon begins to expand, internal pressure within a volume defined by the distensible membrane begins to drop, forcing the device to aspirate a quantity of surrounding blood inside the volume which then begins to coagulate by stasis or some stimulus. The balloon may be configured to automatically release into the aneurysm or vessel or it may be released by a detachable joint.

57 Claims, 13 Drawing Sheets

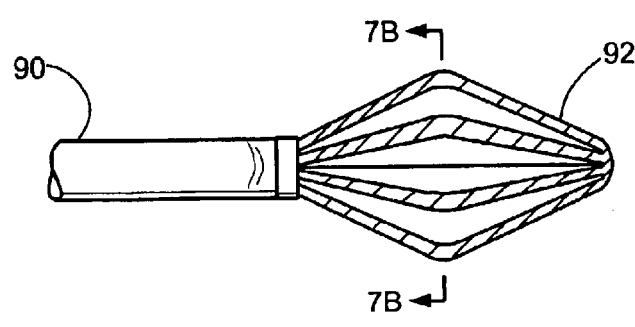
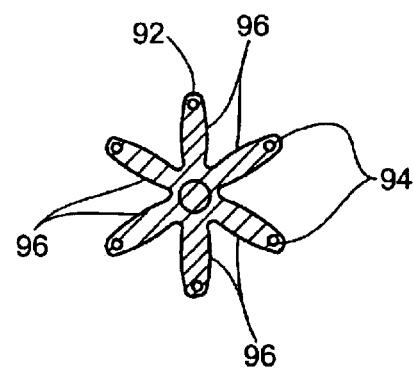
FIG. 7A    FIG. 7B
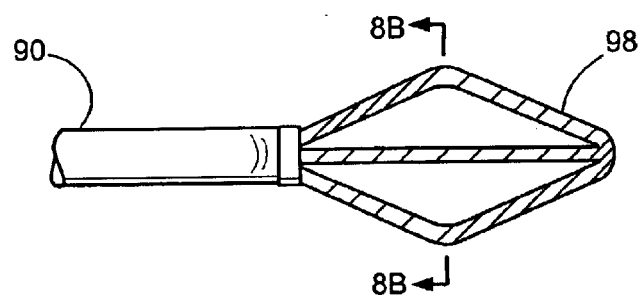
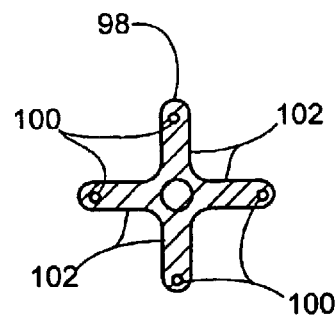
FIG. 8A    FIG. 8B
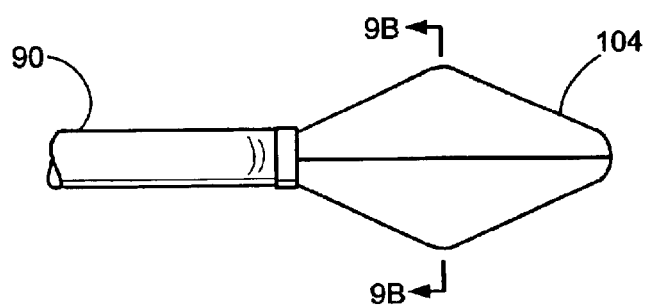
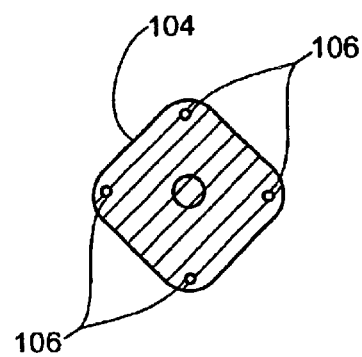
FIG. 9A    FIG. 9B

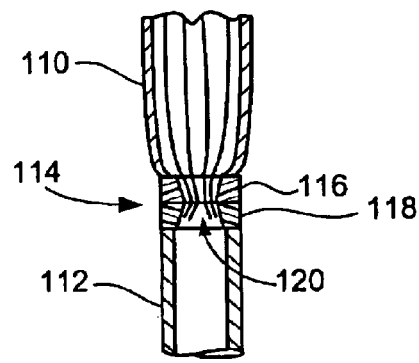
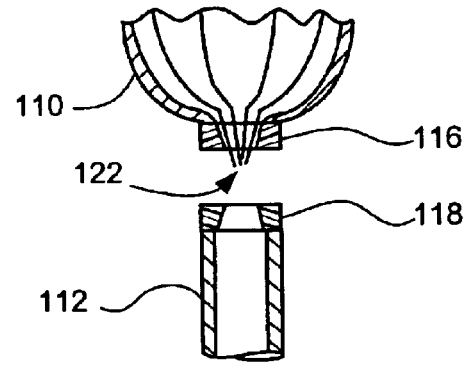
FIG. 10A        FIG. 10B
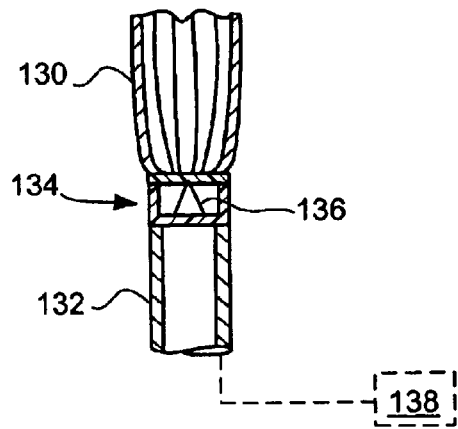
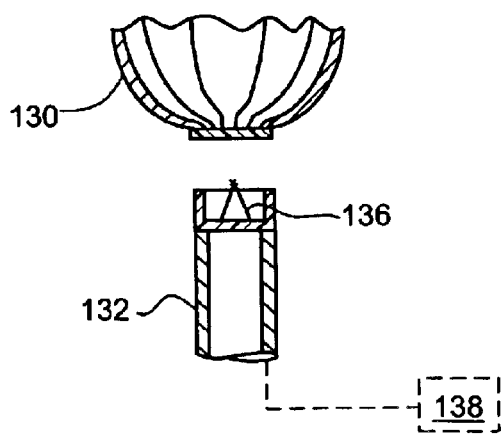
FIG. 11A        FIG. 11B

EMBOLIC BALLOON

TECHNICAL FIELD OF THE INVENTION

The present invention relates generally to devices and methods for the embolization of aneurysms and more particularly to such devices and methods for utilizing detachable balloons.

BACKGROUND ART OF THE INVENTION

Aneurysms have conventionally been treated surgically with varying degrees of success. However, surgical treatment of vascular aneurysms continues to involve a high degree of risk to the patient and can result in surgical mortality and disability.

One method for treating aneurysms that is less traumatic and which reduces or eliminates the need for surgical intervention involved the use of a fixed balloon catheter to artificially embolize the vessel leading to the aneurysms. The non-detachable balloon evolved into a detachable balloon delivered on an intra-arterial flexible catheter and was used clinically as early as 1972. Subsequent clinical work has also used detachable balloons with gradually improving results.

Detachable balloons generally employ three main features: a shell or membrane for containing an inflation medium, a sealing mechanism to close the shell or membrane after detachment of the balloon, and an attachment which maintains a connection to a delivery device until detachment of the balloon is desired. In the past, balloon membranes were fabricated from highly resilient elastic materials such as natural latex which provided an adequate container; however, an inflated balloon formed of latex becomes very hard and does not readily conform to surrounding tissue. Also, some aneurysms have varying shapes for which a spherical balloon may not appropriately fill.

The most commonly used sealing mechanisms employed in the past consisted of a simple elastic "string" tied around the neck of the balloon by each user; however, this has been proved to be unreliable. Improved sealing mechanisms have been used but their complexity or size has prevented them from being used successfully in some vessels, such as cerebral blood vessels which are usually fragile.

Detachable balloons are generally inflated with a suitable fluid, typically a polymerizable resin, and released from the end of the catheter. However, when using intravascular balloon embolization of intracranial berry aneurysms, inflation of a balloon into the aneurysm carries some risk of aneurysm rupture due to possible "overfilling" of portions of the sac and due to the traction produced when detaching the balloon from the end of the catheter.

Moreover, a vascular balloon is difficult to retrieve after the resin within the balloon sets up, and the balloon cannot be easily visualized using radiographic techniques unless it is filled with contrast material. Balloons have also been known to rupture during filling, or release prematurely during filling, or leak monomeric resin into the vasculature during the period before the monomer sets up into polymeric form.

A balloon delivery catheter used for artificial vessel embolization is described in U.S. Pat. No. 4,819,637 to Dormandy, Jr. et al., which is incorporated herein by reference in its entirety. Dormandy describes a detachable balloon delivery catheter which includes a cylindrical valve base and a self-sealing valve mounted on the valve base. However, Dormandy does not show or describe a balloon which can self-expand while aspirating blood within the balloon to form an embolic occlusion within an aneurysm.

U.S. Pat. No. 5,456,666 to Campbell et al., which is incorporated herein by reference in its entirety, describes a medical balloon which can fold into predetermined shapes and is expandable from a folded condition for insertion into the body. However, Campbell likewise does not show or describe a self-expanding balloon which can aspirate blood.

U.S. Pat. No. 5,458,572 to Campbell et al., which is also incorporated herein by reference in its entirety, also describes a balloon which is adapted to be folded into predetermined configurations. The balloon is adapted for inflation from a folded configuration to an inflated, expanded configuration and back to the folded configuration. However, Campbell also does not show or describe a self-expanding balloon which can aspirate blood.

Therefore, there is a need for a balloon device which can adequately conform to the surrounding interior tissue of an aneurysm and also eliminate the dangers of aneurysm rupture due to overfilling of the balloon.

SUMMARY OF THE INVENTION

The present invention describes a detachable balloon system which may expand while aspirating a quantity of surrounding blood to occlude a vessel or aneurysm. The balloon may be capable of treating aneurysms through placement of the detachable balloon directly inside, e.g., an aneurysmal sack, thereby preserving the original artery and blood flow.

The balloon is preferably configured to have a distensible membrane which may define a plurality of orifices throughout its surface. The distensible membrane may be compiised of a variety of materials, e.g., silicone, silicone elastomers, latex, polyurethane, KRATON (Shell Oil Co., Houston., Tex.), etc. Also within the distensible membrane may be a plurality of expandable members. These members are preferably comprised of a shape memory alloy, e.g., Ni—Ti alloy (nitinol), which may be compressed into a first configuration for delivery and insertion, and then expanded into a larger, second configuration. The expandable members may be configured to merely contact an internal surface of the distensible membrane; alternatively, they may also be embedded within the distensible membrane to form an integral device. Alternatively, a structure of expandable members or a single wire made of the shape member alloy may be delivered as a separate structure into the distenible membrane after the membrane has been inserted into the vasculature or aneurysm and then expanded.

The expandable members may be constrained by a delivery sheath or other external force, or they may be configured to automatically expand upon application of a stimulus. Such stimuli may comprise heat (as generated by the body, surrounding vessels, and fluids or by warm water transported through the delivery catheter), electrical energy which may be delivered via wires through the delivery catheter shaft, or RF energy which may be actuated and delivered externally of the body during balloon insertion and expansion.

Once the balloon begins to expand, an internal pressure within the volume defined by the balloon membrane may begin to drop. The drop in pressure may force the device to aspirate a quantity of surrounding blood and fluids inside the volume. Once inside, the blood may undergo coagulation by stasis. Alternatively, blood coagulation may be brought about by introducing a stimulus to the enclosed volume of blood. The stimulus may comprise chemical factors, e.g., thrombin, or an electrical charge may be used to begin the clotting cascade. Once the coagulation is finished, an embolus is created for the potential treatment of aneurysms and vessels.

In the expanded configuration, the device may form a spherical shape; alternatively, non-spherical shapes may be made to accommodate different shaped aneurysms and vessels. Such shapes may comprise disks, elliptical disks, or any other variety of shapes. Also, once in the expanded configuration, the balloon may be configured to automatically release into the aneurysm or vessel or it may be released by a mechanically detachable joint or an electrolytic joint.

Furthermore, optional methods may be used in conjunction to maintain the device within the aneurysm and vessels. For instance, the distensible membrane may be made of a photopolymerizable material. After the device has been placed, a light source may be used in the vasculature to polymerize the membrane. Also, a retaining coil or stent may also be deployed adjacent to, e.g., the aneurysm neck, to prevent the device from becoming dislodged.

BRIEF DESCRIPTION OF THE DRAWINGS

FIGS. 7A–7B show a side view and cross-sectioned end view, respectively, of another variation.

FIGS. 8A–8B show a side view and cross-sectioned end view, respectively, of another variation.

FIGS. 9A–9B show a side view and cross-sectioned end view, respectively, of yet another variation.

FIG. 10A shows a cross-sectioned side view of a variation of a joint attaching an unexpanded device.

FIG. 10B shows the cross-sectioned side view of FIG. 10A with a detached joint releasing the expanded device.

FIG. 11A shows a cross-sectioned side view of a variation of an electrolytic joint attaching an unexpanded device.

FIG. 11B shows the cross-sectioned side view of FIG. 11A with the detached electrolytic joint releasing the expanded device.

DETAILED DESCRIPTION OF THE INVENTION

Several variations are discussed below and with reference to the attached drawings. These descriptions and drawings are for explanatory purposes and do not exhaustively represent all combinations and configurations provided by this invention. Those skilled in the art will readily appreciate that many other variations could be derived originating from these descriptions and cited technical findings without further invention.

Figure 1:
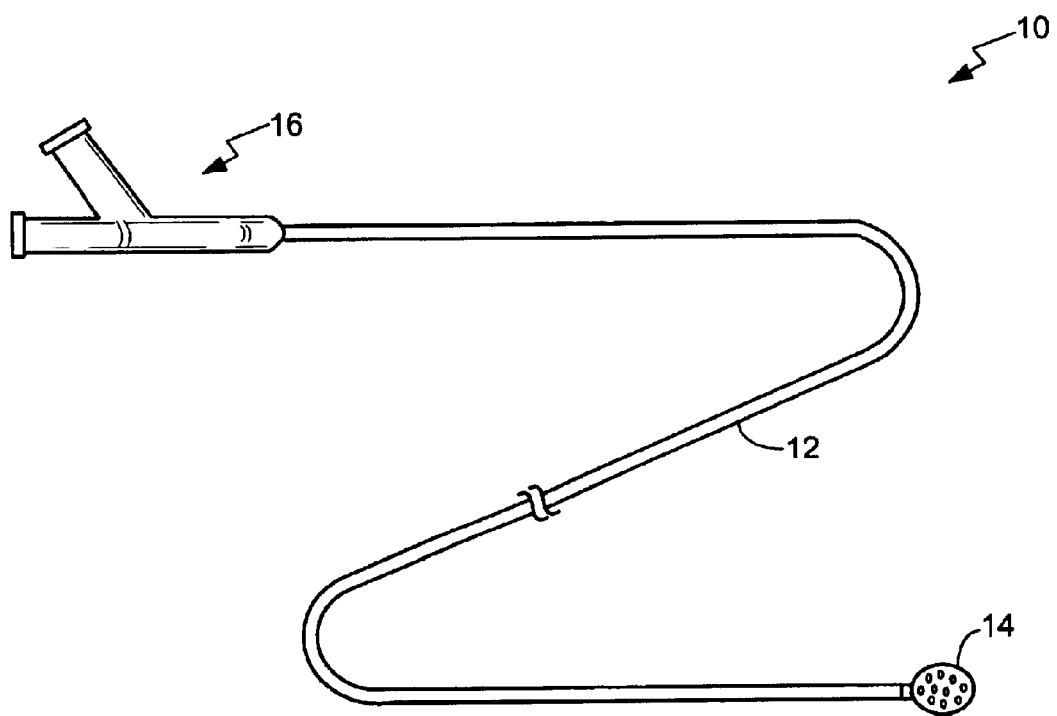
FIG. 1 shows a catheter assembly with a variation of the present invention.

As seen in FIG. 1, a variation of the present invention is shown as balloon device 14 in catheter assembly 10. Assembly 10 may have catheter shaft 12 typically attached to a fluid attachment apparatus, e.g., a Luer-lok assembly 16, or any other desired attachments on a proximal end of catheter 12. At a distal end of catheter 12, balloon device 14 may be attached, as described in further detail below.

Figure 2A:
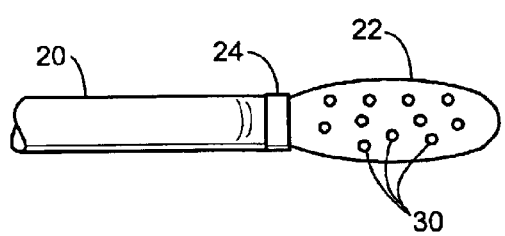
FIGS. 2A and 2B show a side view and a cross-sectioned side view, respectively, of a variation with an unexpanded membrane.
Figure 2B:
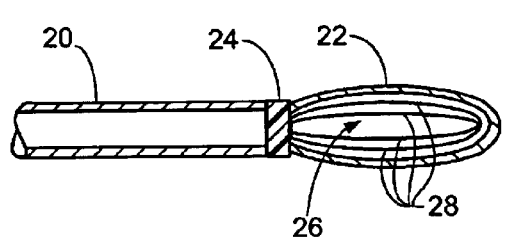

FIG. 2A shows an exterior side view of a variation of the present invention in an unexpanded state. FIG. 2B shows a cross-sectioned side view of the device of FIG. 2A. The present invention may typically be formed into a first compressed or unexpanded configuration for delivery into the vascular system, or more particularly, into an aneurysm. It may then be expanded by a variety of methods, as discussed in further detail below, into a second expanded configuration. The device and its variations discussed herein may provide an expandable embolizing device which may be self-expanding or which may expand upon the application of a stimulus. The rate and shape of the expanding membrane and structure may be customized to provide for gentle expanding forces, thereby minimizing any trauma to surrounding tissue. Among some of its other benefits, the present invention may also potentially eliminate the need for a separate fluid for expanding the device, thereby eliminating problems associated with leakage and deflation of the device.

As seen in FIG. 2A, catheter shalt 20 is shown with distensible balloon membrane 22 which may be attached to shaft 20 by detachable joint 24. Operation and variations on detachable joint 24 will be described in further detail below. Membrane 22 may be comprised of any variety of materials having adequate shear strength and which may allow for distension or expansion to occur without ripping or tearing. Such a material is also preferably biocompatible and flexible enough to be inserted intravascularly and/or into an aneurism without causing trauma to surrounding tissue. Furthermore, membrane 22 is preferably compliant enough to allow the membrane to comply or farm against the surrounding tissue once inserted into a body. Two classes of materials suitable for this device include elastomeric materials and non-elastomeric materials, e.g., polyethylene Membrane 22 may preferably be made from such distensible or elastomeric materials as, e.g., silicone, silicone elastomers, latex, polyurethane, KRATON (Shell Oil Co., Houston, Tex.), etc. Depending upon the material which distensible membrane 22 is made from, membrane 22 may have a varying wall thickness to produce the desired physical properties. The device variation shown as membrane 22 generally will have a wall thickness ranging from about 0.0005 to about 0.0015 inches, and preferably has a thickness of about 0.001 inch. Alternatively, membrane 22 may also be made out of a mesh having a plurality of uniform holes. A wall having too thin of a thickness may potentially rip or tear upon expansion. On the other hand, a wall having too great of a thickness may inhibit or prevent the device from fully expanding into its desired configuration; moreover, it may make it difficult to deliver through a small lumen catheter.

There may be one or more holes or orifices 30 defined over the surface of distensible membrane 22. There may be a single orifice; but a single orifice in membrane 22 would preferably have a larger diameter or cross-sectional area greater than a diameter or area of an orifice where there were several other orifices. Orifices 30, as seen in FIG. 2A, may have a diameter ranging from about 0.0001 to about 0.010 inches, and is preferably about 0.005 inches. These orifices 30 may define passageways between the exterior of the device and an interior lumen or volume 26 which is defined by the enclosed membrane 22, as seen in FIG. 2B. Distensible membrane 22 and orifices 30 may be manufactured by a variety of methods. A preferable method is to coat a ball or ovoid made from wax, or other material having a relatively low melting temperature, with the membrane 22 material. The ball or ovoid preferably has a shape and diameter of the final desired membrane 22 shape. The membrane 22 material may be left on the ball or ovoid to polymerize. Orifices 30 may then be created by applying focused pulses of laser energy to the polymerized material. Alternatively, orifices 30 may also be mechanically produced by simply puncturing the material with a puncturing device having an extremely sharp and small-diameter tip. Finally, the wax material may then be melted and extracted from interior lumen or volume 26 through the main opening or through orifices 30.

Within volume 26, there may be enclosed or encapsulated several expandable ribs or members 28. These expandable members 28 are preferably attached and anchored in joint 24 and extend out within volume 26 to form an interior structure. The number of expandable members 28 may range from a single loop anchored in joint 24 to several expandable members 28, depending upon the desired form of expansion of membrane 22. Expandable members 28 may be configured to expand from a compressed or unexpanded configuration by one or more modes of expansion. For example, expandable members 28 may be self-expanding upon the release of a restraining force; or they may be mechanically expandable; or alternatively, they may also be expandable upon a temperature change.

Expandable members 28 are preferably pre-formed of a biocompatible shape memory alloy, e.g., Ni—Ti (nitinol). Such a material choice enables expandable members 28 to be formed into a first compressed shape, as shown in FIGS. 2A–2B, for insertion into a vessel lumen or aneurysm. Thus, once the device is disposed or placed at a desired location in its compressed configuration, expandable members 28 may be self-expanding without the need of a stimulus. Alternatively, expandable members 28 may be expanded from its compressed shape upon the application of a transformation factor or stimulus applied to the device. The stimulus may be any practical type of stimulus. For instance, the heat transferred generally by the body or by the vessel lumen and blood or fluids may be a sufficient stimulus to trigger the transformation of expandable members 28 upon exposure. Another stimulus may be electrical energy which may be supplied via a wire electrically connected to expandable members 28 and actuated from outside the body. Still another form of energy may be RF energy which may be delivered to expandable members 28 from outside the body. And yet another example of a possible stimulus is a small quantity of warm water which may be injected via catheter shaft 20 into volume 26 and into contact with expandable members 28.

Figure 3A:
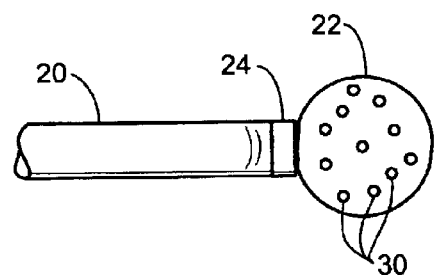
FIGS. 3A and 3B show a side view and a cross-sectioned side view, respectively, of the variation shown in FIGS. 2A and 2B with an expanded membrane in a spherical shape.

Exposure to the stimulus preferably causes expandable members 28 to then expand into a second expanded shape, i.e., its desired pre-formed shape or configuration, shown in the variation of FIG. 3A as a spherical shape. Alternatively, expandable members 28 and distensible membrane 22 may be constrained by, e.g., an outer sheath, tube, exterior catheter, or some external force, and held in an unexpanded configuration. When the constraining element or force is removed, expandable members 28 may be free to expand into the larger expanded configuration within an aneurysm without the need for an external stimulus. In the expanded configuration, the device preferably presses gently against the vessel or aneurysm walls. Expandable members 28 are preferably designed to expand outwardly with a very gentle force to prevent any trauma, e.g., puncturing, to the adjacent vessel or aneurysm tissue in which the device is expanding. This may be accomplished in one way by configuring expandable members 28 to expand slowly such that the device and, e.g., the aneurysm walls, come into contact in a gentle manner. Alternatively, because aneurysms in different patients and different locations will vary in size, a properly sized distensible membrane 22 may be selected for insertion by size matching. For example, for an aneurysm having a diameter of 0.300 inches, a balloon having a diameter of 0.250, 0.300, or 0.350 inches may be inserted depending upon the desired results. To accommodate the range, the surgeon or physician may have an array of balloons available with different diameters ranging in increments.

Figure 3B:
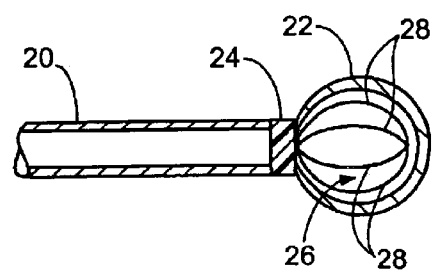

FIG. 3B, which is a cross-sectional view of the device of FIG. 3A, shows expandable members 28 in the expanded configuration. Expandable members 28 may be embedded or encapsulated within distensible membrane 22 to form an integral membrane structure, but they may preferably simply contact an interior surface of membrane 22. When expandable members 28 expand, they preferably push out against the interior surface of distensible membrane 22 to expand it into the desired configuration. During insertion into the vessel or aneurysm and prior to this expansion, volume 26 in FIG. 2B is at some internal pressure, typically ambient. However, during the expansion, the internal pressure in volume 26 seen in FIG. 3B is reduced to some pressure less than ambient. This pressure reduction causes the device to aspirate a quantity of blood or fluid surrounding distensible membrane 22 into volume 26.

Once the quantity of blood is aspirated into volume 26, the blood may then be coagulated by a variety of methods. One method is to simply allow the coagulation to occur by stasis within volume 26. Another method is to introduce an electrical charge into the aspirated blood via a wire electrically connected to within volume 26 to begin the clotting cascade. Still yet another method for inducing coagulation is chemically by introducing a chemical factor, e.g., thrombin, fibrin, platelet extracts, etc., into volume 26 after or during aspiration of the blood. And yet another method is by mechanically inducing coagulation by introducing fibers or coating the volume 26 interior or expandable members 28 with platinum.

After insertion of the device and once the aspiration has begun or has completed, the balloon distensible membrane 22 may be released via releasable joint 24. This joint may be a mechanically releasable joint actuated by the physician or surgeon after the expansion of membrane 22 has occurred, or it may be actuated and released automatically upon the fall expansion of expandable members 28. Another variation of joint 24 may include an electrolytic joint which may be electrically dissolved just prior to release. Various joints will be discussed in greater detail below. Once the coagulation is completed, the expanded device, or balloon, may act as an embolus. If inserted into an aneurysm, the embolic balloon may then succeed in clotting the aneurysm and prevent any further enlargement thereof.

Figure 4A:
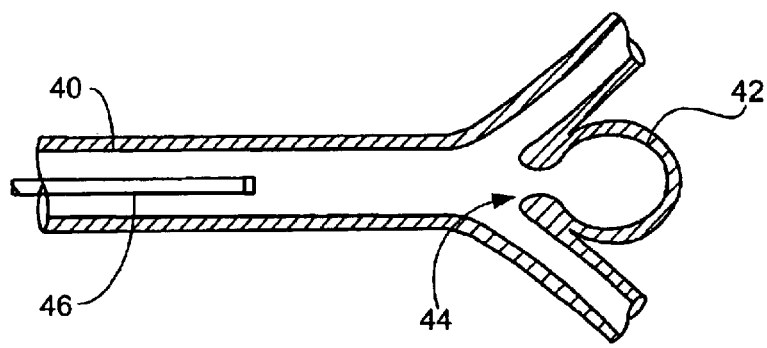
FIGS. 4A–4D show the delivery and insertion of a variation of the device into an aneurysm.
Figure 4B:
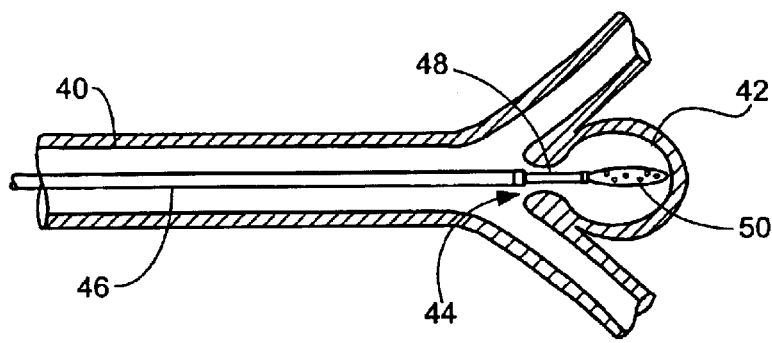
Figure 4C:
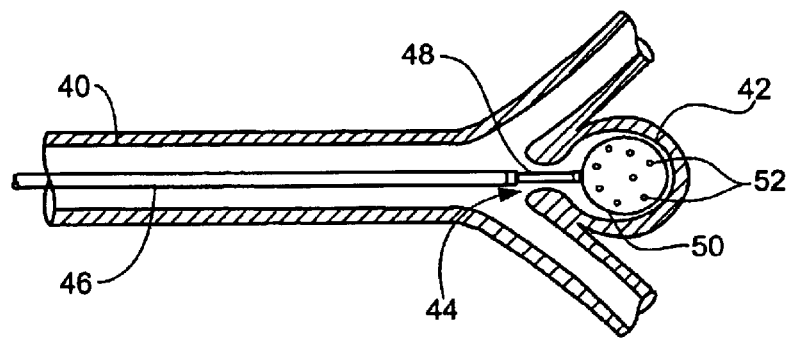
Figure 4D:
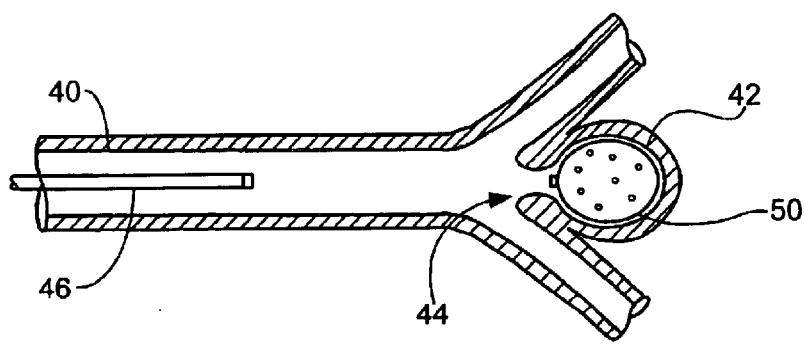

A representative method of inserting and deploying the device is shown in FIGS. 4A–4D. FIG. 4A shows a bifurcating artery/vessel 40 with aneurysm 42, which defines a neck or opening 44, formed at the junction (e.g., a "Charcot Berry"). Insertion catheter 46 may be advanced through the vasculature and through vessel 40 towards aneurysm 42. FIG. 4B shows insertion catheter 46 near aneurysm opening 44 while inserting a variation of the present invention, embolic balloon 50 in an unexpanded configuration, as described in FIG. 2A. As shown in the figure, embolic balloon 50 may be delivered into aneurysm 42 while attached to delivery catheter 48. Once free of any constraints, embolic balloon 50 may then be free to expand on its own or via a stimulating factor, as described above. In FIG. 4C, embolic balloon 50 is shown in its expanded state. During the expansion, blood and fluids surrounding embolic balloon 50 in aneurysm 42 may be aspirated through orifices 52 and into balloon 50. Also during the expansion, embolic balloon 50 is shown as remaining attached to delivery catheter 48 although balloon 50 may alternatively be released from delivery catheter 48 during the expansion once balloon 50 becomes too large to inadvertently escape through opening 44. During the expansion process or shortly thereafter, the blood which has been aspirated is then preferably coagulated by any one of the methods described above. Finally in FIG. 4D, as balloon 50 has completed its expansion and/or coagulation process, balloon 50 may be released from delivery catheter 48 and both catheters may then be withdrawn from the vasculature.

Figure 5A:
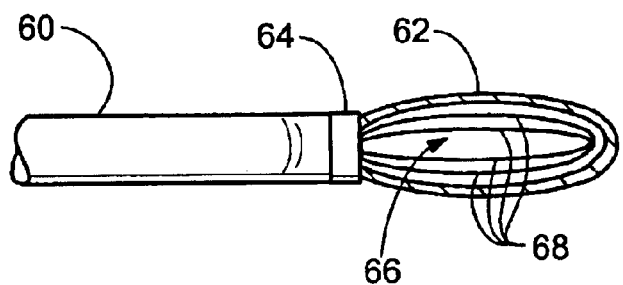
FIGS. 5A–5C show a cross-sectioned side view of the expansion of another variation of the device having a disk shape.
Figure 5B:
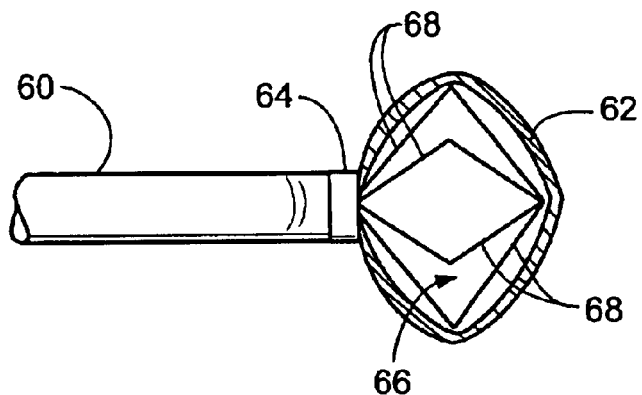
Figure 5C:
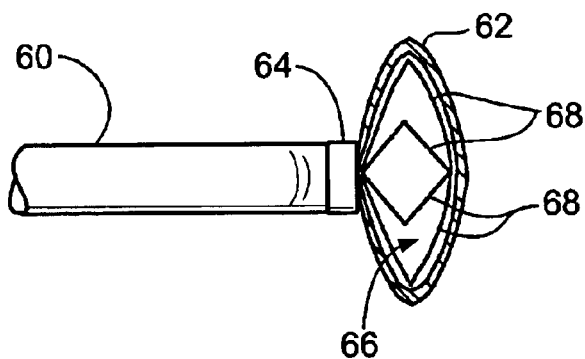

An alternative variation for the balloon configuration is shown in FIGS. 5A–5C where the device may expand into a disk shape. As shown in FIG. 5A, an unexpanded cross-section of distensible membrane 62 is attached to catheter shaft 60 via joint 64. Distensible membrane 62 is shown surrounding expandable ribs or members 68 and enclosing volume 66. FIG. 5B shows expandable members 68 undergoing expansion into an intermediate disk shape and FIG. 5C shows the fully expanded members 68 and distensible membrane 62 in the form of a disk or squashed disk. This variation may be configured to aspirate surrounding blood or fluids and undergo coagulation in the same manner as described above. Aside from spheres and disks, the distensible membrane and expandable members may be configured to form a variety of shapes. For example, the cross-sectional shapes of these various configurations may be designed to become circles, ellipses, various stars and rectangles, and also squares.

Figure 6:
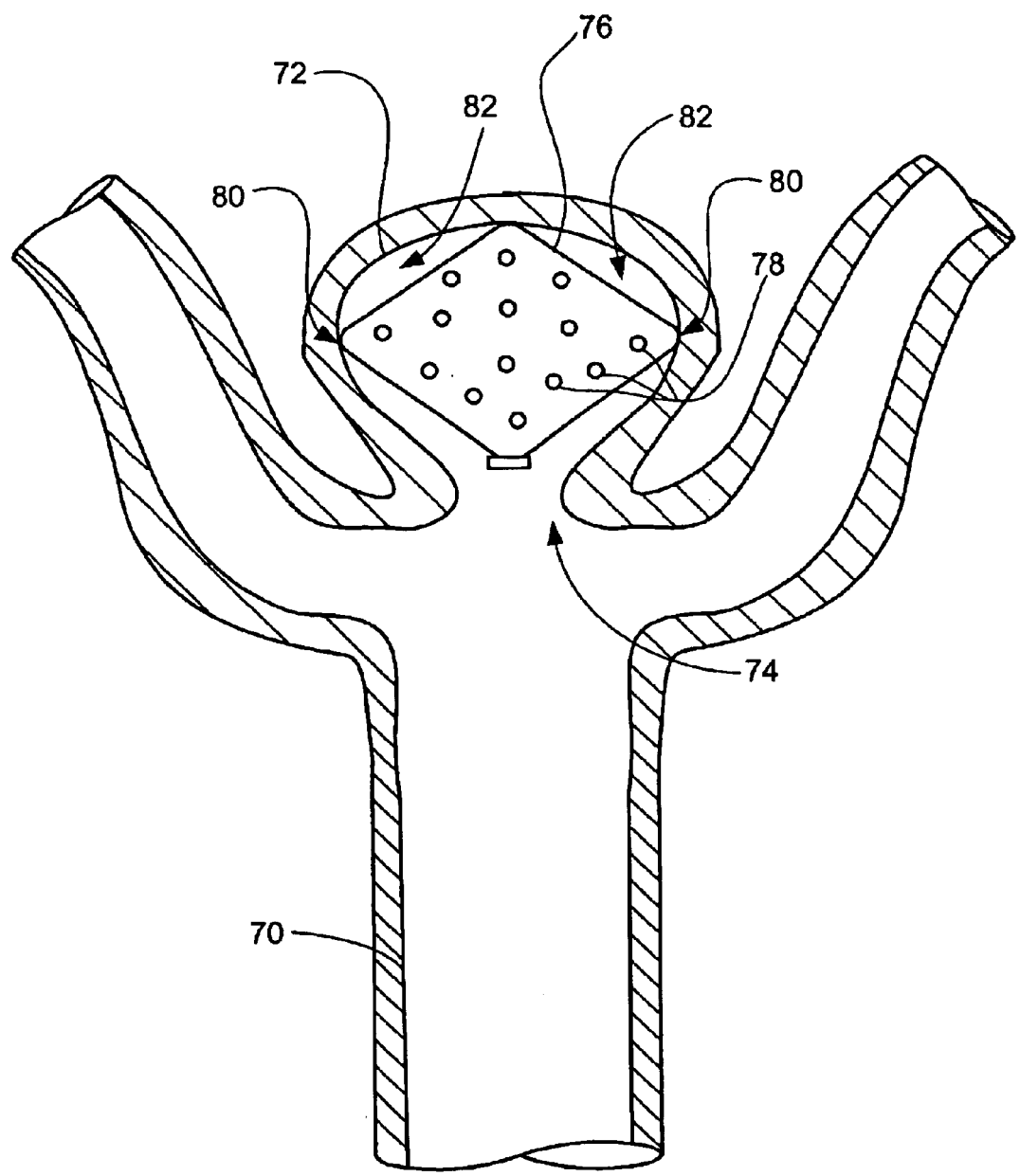
FIG. 6 shows a side view of the device of FIGS. 5A–5C within an aneurysm.

The variation shown in FIGS. 5A–5C may be useful in applications where the aneurysm has a non-spherical shape. For example, FIG. 6 shows the variation expanded in aneurysm 72. Balloon 76 may be delivered through vessel or artery 70 and inserted through aneurysm neck or opening 74. Once balloon 76 is inserted into aneurysm 72, it may be expanded by any of the methods discussed above. While balloon 76 expands, the surrounding blood or fluid may be aspirated through orifices 78 and enter within the interior of balloon 76, where the blood or fluid may then be coagulated. As balloon 76 expands, its outermost diameter may expand and contact a peripheral region 80 of the aneurysm 72 interior. The contact may halt the expansion of balloon 76 and also create an enclosed volume 82 between balloon 76 and an interior wall of aneurysm 72. The blood or fluid trapped in enclosed volume 82 may then also undergo coagulation to further prevent aneurysm 72 from expanding further.

As discussed above, the expandable members may be embedded or encapsulated within or merely placed within the distensible membrane to provide mechanical structure to the overall device, preferably in the form of an integral membrane structure. Also, during delivery and prior to expansion, the expandable members and distensible membrane may be folded into a variety of configurations to facilitate delivery and insertion into the vessel or aneurysm. FIG. 7A shows a side view of balloon 92 in an unexpanded state attached to catheter shaft 90. FIG. 7B shows cross-section 7B–7B from FIG. 7A. As seen, expandable members 94 (in this variation, there are six members) may be embedded into the distensible membrane of balloon 92 and the balloon may be folded and compressed in such a way as to form individual arms 96. Once expandable members 94 are expanded, balloon 92 may take the form of any of the shapes discussed herein. FIG. 8A shows another variation in the side view of balloon 98. FIG. 8B shows cross-section 8B—8B taken from FIG. 8A where balloon 98 is seen having four expandable members 100 embedded in the distensible membrane to form individual arms 102 when balloon 98 is in a compressed, unexpanded state. In a further variation, FIG. 9A shows the side view of balloon 104. FIG. 9B shows cross-section 9B—9B taken from FIG. 9A where balloon 104 has expandable members 106 embedded within. In this variation, rather than being folded into individual arms, balloon 104 may be compressed into a rectangular or square shape. When balloon 104 expands, the distensible membrane may then expand by stretching or distending into the desired configuration.

Once the distensible membrane is expanded, the balloon may be released into the vessel or aneurysm. The balloon may be released by a releasable joint, as shown in FIG. 10A. Distensible membrane 110 is shown in an unexpanded configuration attached to catheter shaft 112 by detachable joint assembly 114. In this variation, joint assembly 114 is shown comprising upper joint 116 and lower joint 118 being held together by releasable hooks 120, which may be the proximal ends of the expandable members and may also be made of a shape memory alloy, as discussed above. Releasable hooks 120 may be attached to upper joint 116. As shown in FIG. 10B, once the expandable members are expanded, releasable hooks 120 may automatically release from lower joint 118 as they transform to a different configuration into, e.g., released hooks 122. An automatic release mechanism may be possible if hooks 120 are made of the same shape memory alloy and preconfigured to expand into released hooks 122. A single hook made of a shape memory alloy, e.g., nitinol, may also be used to transform from the hooked shape to a straight wire for releasing the joint. Although hooks are shown in this variation, other mechanical fastening devices may be utilized, e.g., barbs, keyed couplings, and friction-fitted couplings.

Aside from mechanically detachable joints, electrolytic joints may also be utilized, as described in U.S. Pat. No.

5,423,829 to Pham et al., which is incorporated herein by reference in its entirety. As shown in FIG. 11A, distensible membrane 130 is shown in the unexpanded configuration attached to catheter shaft 132 by detachable joint assembly 134. Joint assembly 134 in this variation comprises electrolytic joint 136. An electric current may be sent through electrolytic joint 136 via wires (wires not shown) running through the length of catheter shaft 132 and attached to a conventional voltage source 138, which may be actuated from outside the body by a physician, surgeon, nurse, or technician. Once distensible membrane 130 is expanded, voltage source 138 may be actuated to release electrolytic joint 136, as shown in FIG. 11B.

Alternative detachable joints may also include joints held together by a laser-meltable adhesive or glue. Such joints may be released upon the application of laser pulses, delivered via a catheter, which would then melt the adhesive.

Figures 12A, 12B, 12C:
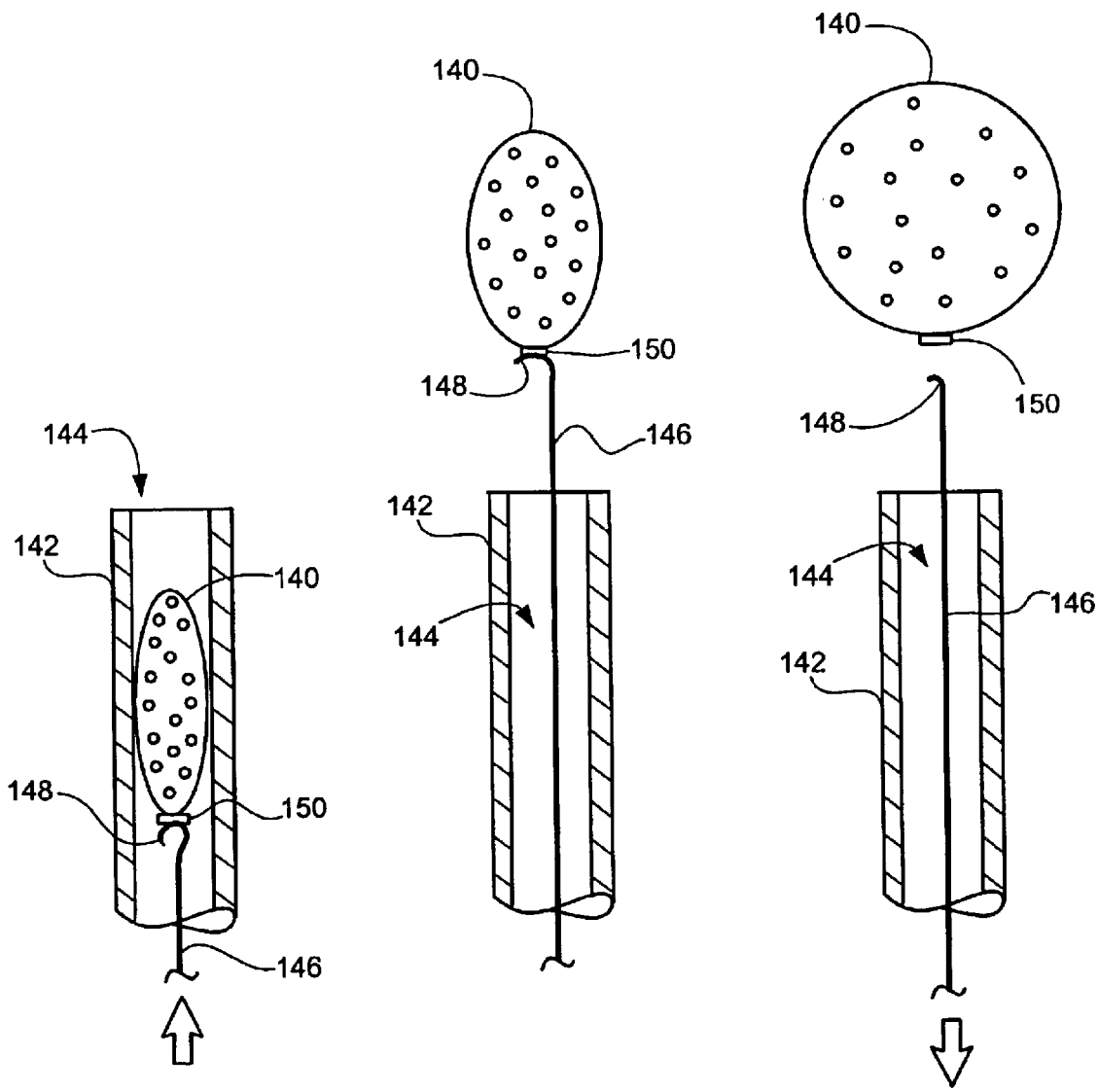
FIGS. 12A–12C show a cross-sectioned side view of a further variation where the device is delivered through a catheter and released upon expansion.

Applications of the present invention may also be embodied in various other designs and modifications. FIG. 12A shows a variation where distensible balloon membrane 140, which may already have the expandable members within, may be held and delivered within delivery lumen 144 of catheter 142. Membrane 140 may be held in place for delivery, as shown in FIG. 12A, and once properly positioned, it may then be urged out of lumen 144 by retaining wire 146, as shown in FIG. 12B. Membrane 140 may be held by wire 146 having a distal end in the form of releasable hook 148 which may retain membrane 140 by attachment 150. Once membrane 140 has been removed from lumen 144, it may undergo expansion and aspirate the surrounding blood or fluid, as described above. Simultaneously, hook 148 may also undergo a change of shape, as seen in FIG. 12B. Wire 146 is preferably made of a shape memory material, e.g., nitinol, so that hook 148 may be preconfigured to form a released hook either automatically or upon application of a stimulus, such as heat emitted by the surrounding fluids and vessels or any of the other stimuli discussed above, at the time of membrane 140 release, as shown in FIG. 12C. As further seen in FIG. 12C, once membrane 140 has been fully expanded and hook 148 fully extended, membrane 140 may be released into the vessel or aneurysm and wire 146 may be retracted and catheter 142 removed from the area.

Figure 13:
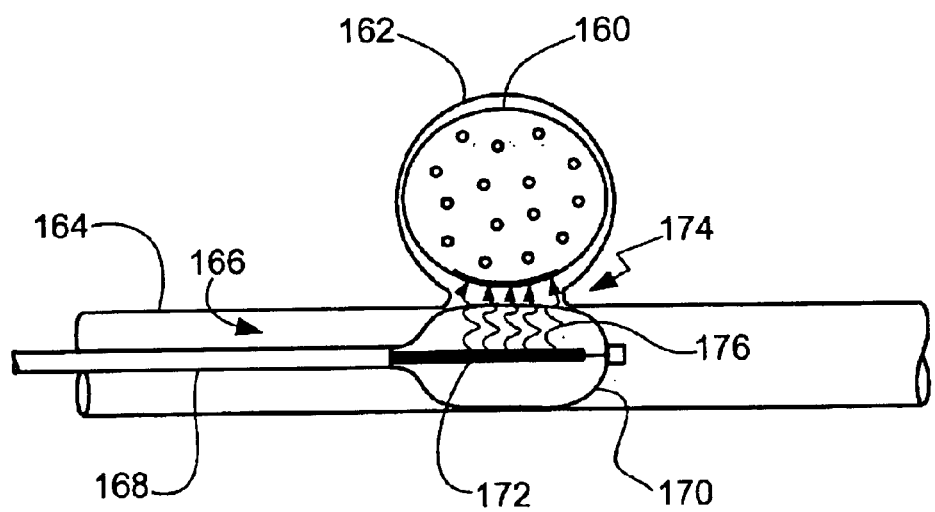
FIG. 13 shows a photopolymerizable version of the device.

Typically, once a balloon device has been placed within an aneurysm, the expanded size and eventual coagulation within the aneurysm help keep the balloon in position. However, in the case of aneurysms having wide necks or openings, the possibility may exist for a balloon being dislodged prior to the coagulation taking effect. In such instances, preventative measures may be incorporated. As shown in FIG. 13, one such measure may include making the balloon membrane 160 out of an ultraviolet light curable or photopolymerizable material. Membrane 160 may be placed within aneurysm 162 and expanded to closely approximate the aneurysm 162 interior. An expandable "molding" balloon 170 may then be inserted into vessel 164 through vessel lumen 166 via catheter 168 so that balloon 170 is placed preferably adjacent to aneurysm neck opening 174. Such positioning may allow expanding balloon 170 to mold or compress part of membrane 160 to conform partly to aneurysm neck 174. Preferably disposed within or on balloon 170 is light delivery channel 172. As balloon 170 is compressed against membrane 160 or when balloon 170 is deflated, ultraviolet or white light 176 may be delivered through channel 172 to at least partially cure membrane 160 to prevent membrane 160 from becoming dislodged from aneurysm 162.

Figure 14:
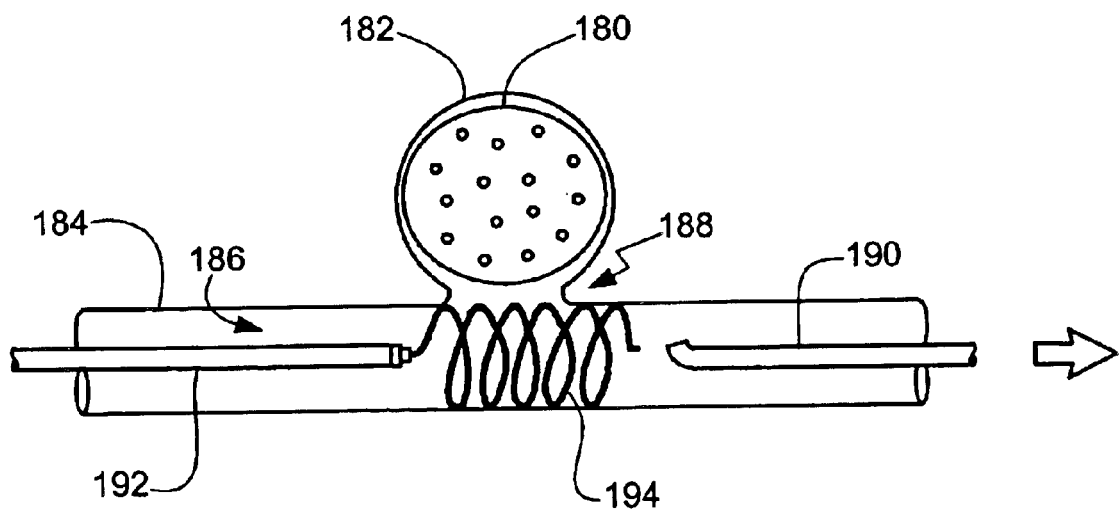
FIG. 14 shows a temporary retaining coil or stent which may optionally be deployed to maintain the device within the aneurysm.

FIG. 14 shows another measure which may be used to prevent distensible membrane 180 from becoming dislodged from aneurysm 182. After balloon 180 has been placed by balloon delivery catheter 190, temporary stent/retaining coil 194 may be delivered via stent/coil delivery catheter 192 through vessel 184 and placed adjacent to aneurysm neck 188. Retaining coil 194 is preferably made of a shape memory material, e.g., nitinol, such that upon delivery, coil 194 may expand to form a coiled shape which is disposed within vessel lumen 186 and may be held in place by self-expansion against the interior wall of lumen 186. Coil 194 may help to retain balloon 180 until coagulation is complete, then coil 194 may then be removed from vessel 184 or left as a permanent implant. Alternatively, coil 194 may be first placed adjacent to aneurysm neck 188 and then balloon 180 may be placed inside aneurysm 182 by being passed between and through the turns of the coil.

Figure 15A:
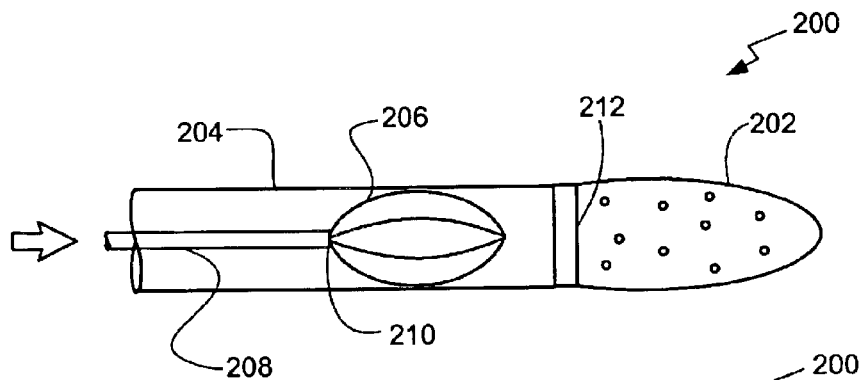
FIGS. 15A–15D show the expandable members as a separate structure which may be inserted into the unexpanded membrane.
Figure 15B:
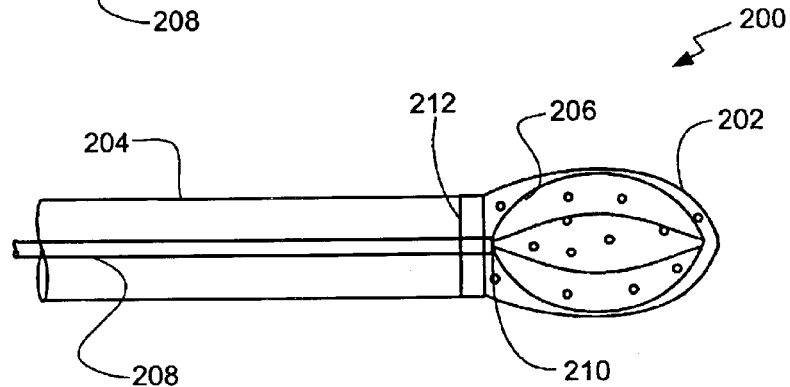
Figure 15C:
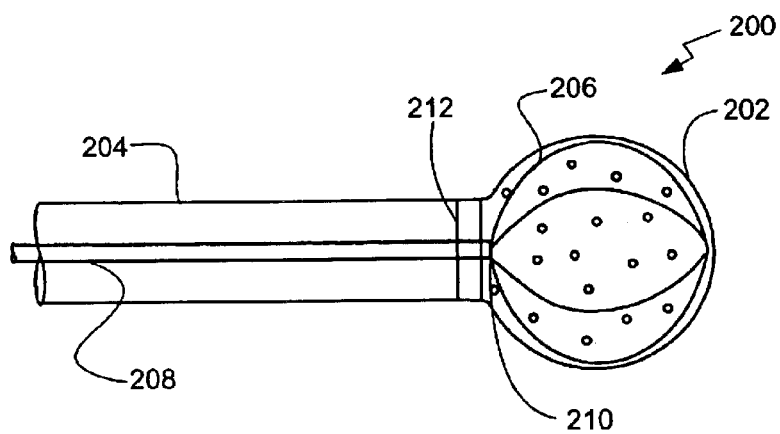
Figure 15D:
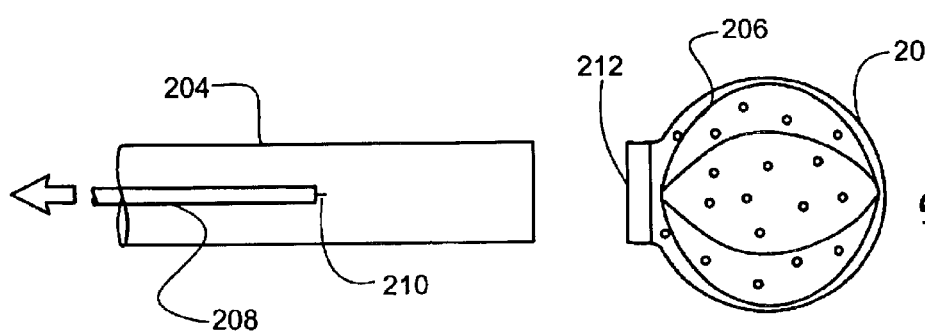

Rather than having the internal expanding ribs or members formed interiorly to the balloon membrane, they may alternatively be inserted within the balloon membrane as a separate structure. Having the expanding members inserted separately may allow the catheter structure, particularly the balloon membrane structure, to have a smaller delivery profile. This smaller profile may also be accomplished by, e.g., winding the balloon membrane about itself. FIG. 15A shows balloon assembly 200 with distensible balloon membrane 202, shown in this variation without any expandable ribs or members within, attached to catheter shaft 204. Such a structure may be delivered and placed within an aneurysm for expansion. A structure of expandable ribs or members 206 may then be inserted through catheter 204 by delivery shaft 208. As seen in FIG. 15B, once expandable members 206 have been delivered into membrane 202 through balloon opening 212, expandable members 206 may then begin to expand as described above. FIG. 15C shows the completed expansion and FIG. 15D shows membrane 202 and expandable members 206 after they have been released from delivery shaft 208 by detachable joint 210. Detachable joint 210 may be any of the joints described above in detail. After the release of expandable members 206, opening 212 may be sealed by a self-closing flap which may shut after delivery shaft 208 is withdrawn.

Figure 16A:
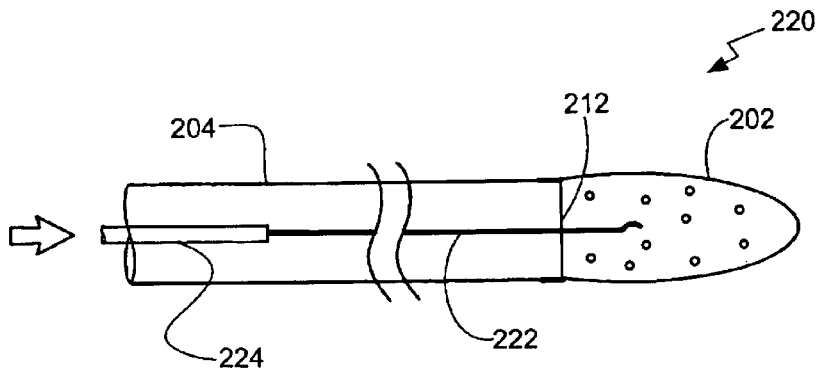
FIGS. 16A–16D show the expandable member as a single wire which winds into a coil upon insertion into the membrane for expanding the membrane.
Figure 16B:
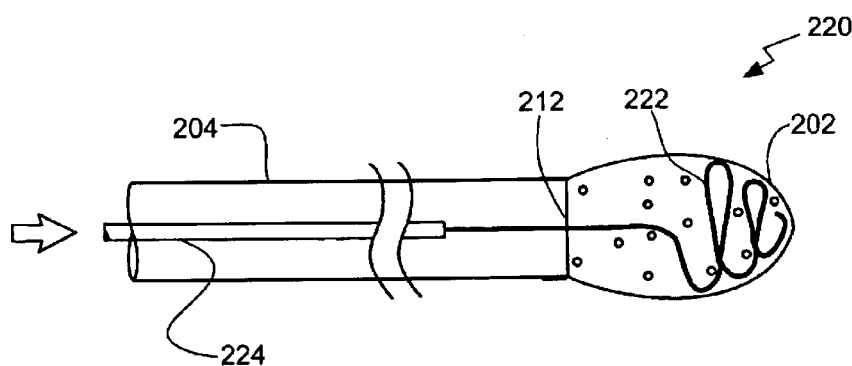
Figure 16C:
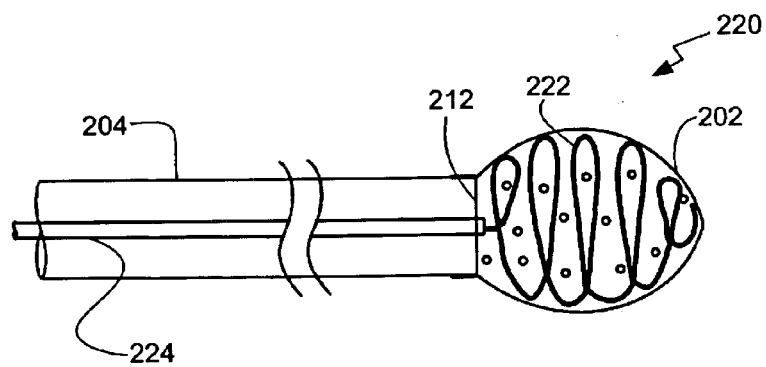
Figure 16D:
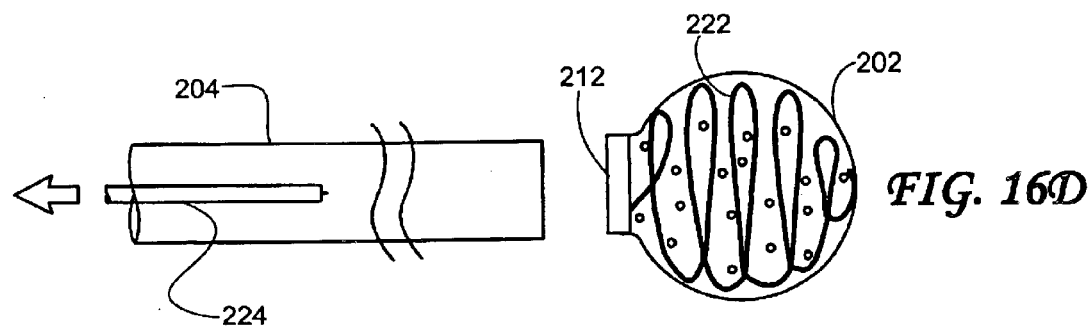

FIG. 16A shows single-wire balloon assembly 220 which is similar to the assembly as shown in FIGS. 15A–D. In this variation, single expandable wire 222 may be delivered via delivery shaft 224 and inserted into balloon membrane 202 through catheter 204. Wire 222 is preferably made of a shape memory alloy, e.g., nitinol, and may be preconfigured to expand into a coiled configuration, as shown in FIG. 16B. As seen in FIG. 16C, as more of wire 222 is placed within membrane 202 and coils up, the expanding wire/coil 222 may then begin to expand membrane 202 so that expansion of membrane 202 occurs in a manner similar to that described above. Finally, as seen in FIG. 16D, once wire/coil 222 is completely placed within membrane 202, the balloon may be released into the aneurysm or vasculature and delivery shaft 224 and catheter 204 may be removed from the area. Opening 212 may again be closed by a self-sealing flap with shuts upon removal of delivery shaft 224 from membrane 202.

Wire/coil 222 is preferably formed of a shape memory alloy, as mentioned above, and it may optionally be covered or coated with a radiopaque material as a visual aid under a fluoroscope during placement and insertion. One variation includes coating wire/coil 222 or wrapping a second coil about wire/coil 222 with a material such as platinum.

Figure 17A:
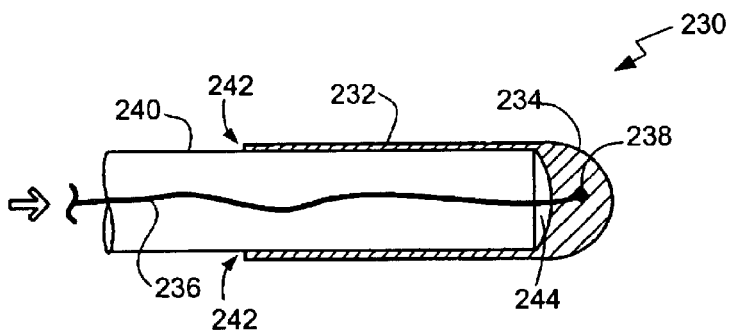
FIGS. 17A–17D show a version of the device as a self-expanding balloon assembly which may be filled with a fluid and an expandable coil to expand the distensible membrane.

FIG. 17A shows self-expanding balloon assembly 230 in a non-expanded state. This variation has expanding membrane 232 fitted tightly over a distal end of catheter shaft 240. Expandable wire 236 extends through catheter shaft 240 from a proximal end of shaft 240 to anchoring region 234 which is disposed in a distal end of membrane 232. Wire 236 may be attached to wire anchor 238 which is located in anchoring region 234. For membrane 232 expansion to occur, hydraulic pressure may be applied from within catheter 240 to begin filling balloon lumen or volume 244 with a fluid, preferably saline or water. This hydraulic pressure may be controlled by a device or reservoir, as discussed in further detail below, preferably located at a proximal end of catheter 240 outside of a patient's body.

Figure 17B:
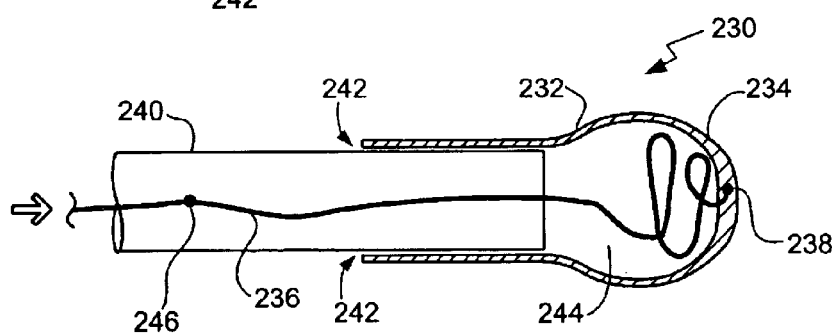

As fluid is pumped into balloon volume 244, it may seep in-between membrane 232 and catheter shaft 240 creating gap 242. As shown in FIG. 17B, the creation of gap 242 and the hydraulic pressure within balloon volume 244 would allow membrane 232 to slide distally away from the distal end of catheter shaft 240. The sliding of membrane 232 would then draw wire 236 into volume 244 because of wire anchor 238. Wire 236 is preferably made of a shape memory alloy, e.g., nitinol, and is preferably preconfigured to expand into a coiled shape in much the same manner as wire 222 shown in FIGS. 16A-16D. As more fluid and more of wire 236 enter volume 244, membrane 232 may begin to expand as it slides off catheter 240.

Figure 17C:
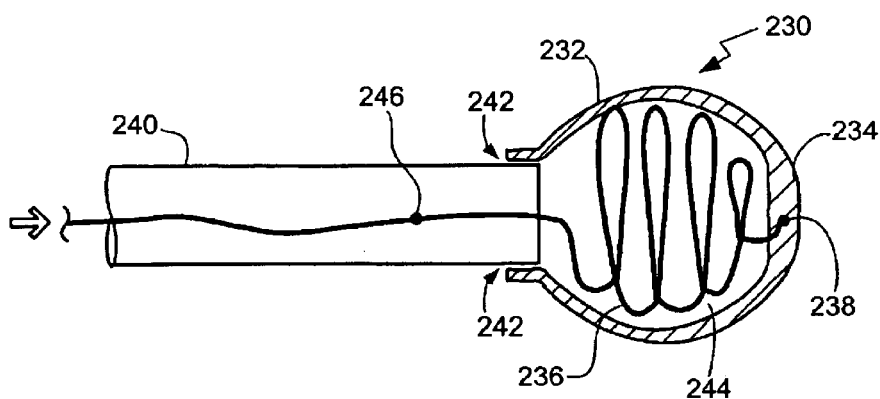
Figure 17D:
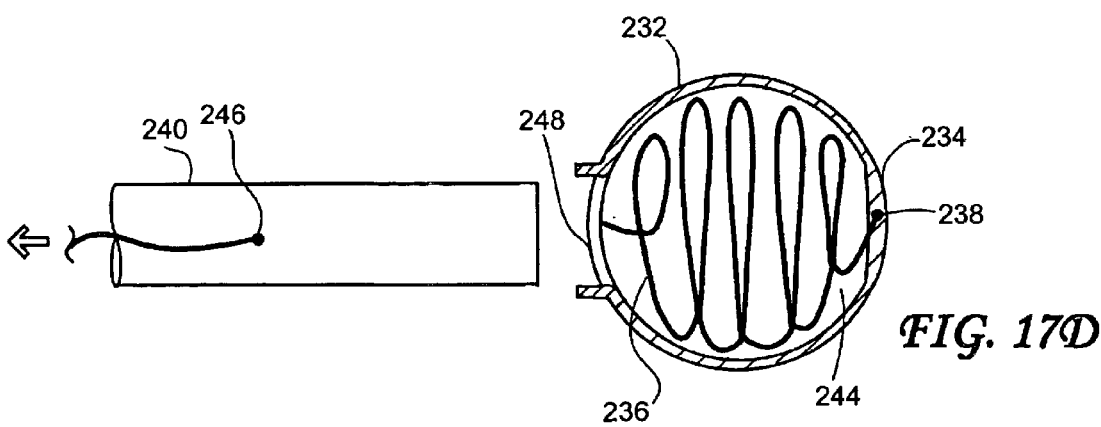

FIG. 17C shows membrane 232 in an almost completely expanded state. As most of wire 236 becomes enclosed and expanded within volume 244, it may be released via detachable joint 246. Detachable joint 246 may be any one of the joints as described above. As shown in FIG. 17D, after wire 236 has been released from joint 246 and is completely within volume 244, joint 246 may be withdrawn from balloon opening 248 and pumping of the fluid may cease. Membrane 232 may be released into, e.g., an aneurysm, and opening 248 may then be closed by a flap in a manner described above.

Figure 18:
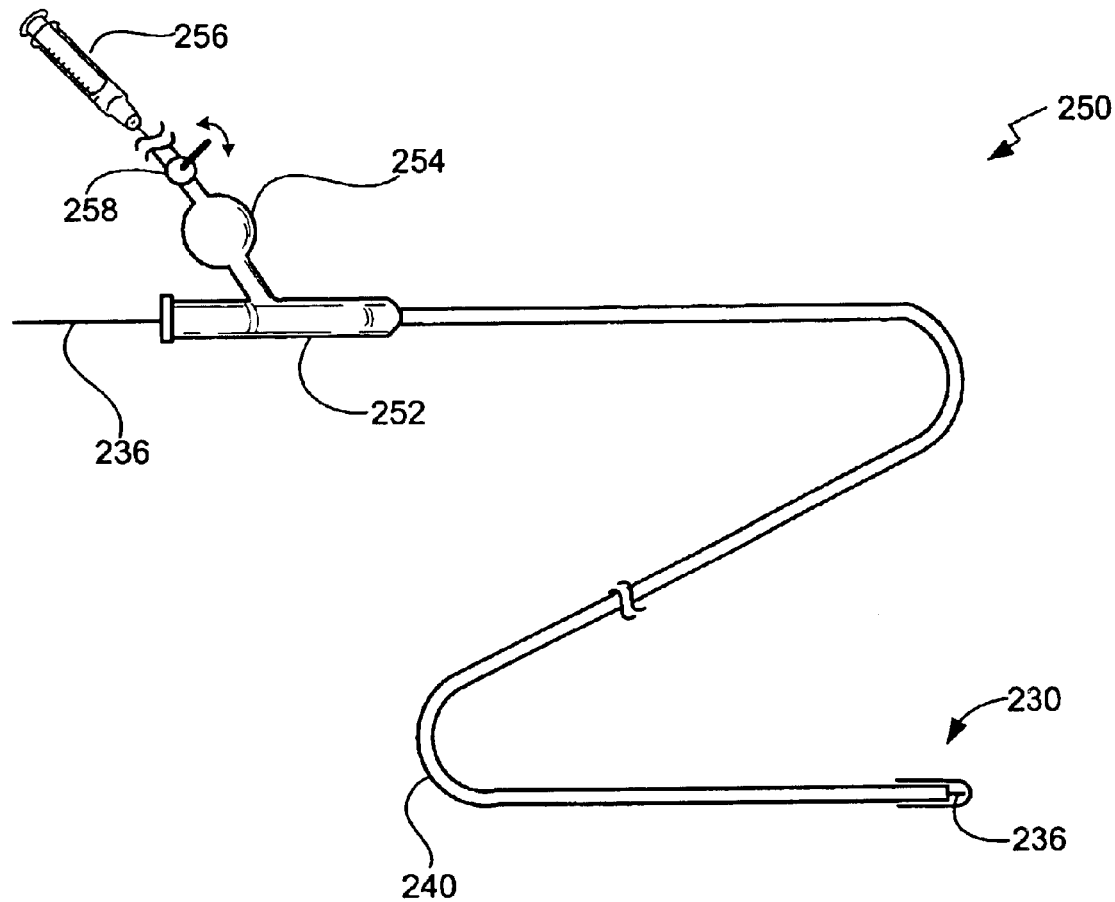
FIG. 18 shows a catheter assembly having a catheter shaft attached to a fluid delivery attachment at a proximal end and to the self-expanding balloon assembly at a distal end.

FIG. 18 shows catheter assembly 250 having catheter shaft 240 attached to a fluid delivery attachment, e.g., a Luer-Lok assembly 252, at a proximal end and to the self-expanding balloon assembly 230, as shown in FIGS. 17A-D, at a distal end. Because fluid is preferably pumped into assembly 230, it may require a pressure regulation system or device. An exemplary device is shown where attachment 252 may be attached in fluid communication to an optional compliance reservoir 254. Reservoir 254 may also be connected to a pump or some type of fluid injector 256, e.g., a syringe filled with the fluid. During use, fluid injector 256 may be used to pump the fluid through adjustable valve 258, which is optional and may be used to control the pressure head or flow rate of the fluid being pumped through it, and into compliance reservoir 254, which may be used to maintain a constant fluid pressure in catheter 240 and balloon assembly 230.

The applications of the embolic balloon discussed above are not limited to the treatment of aneurysms, but may include any number of vascular maladies. Modification of the above-described methods for carrying out the invention, and variations of the mechanical aspects of the invention that are obvious to those of skill in the art are intended to be within the scope of the claims.

I claim:

1. An embolizing device for insertion into an aneurysm, comprising:

at least one detachable self-expanding member configured to be sealed within an elastomeric membrane which is adapted to distend by stretching into compliant contact within the aneurysm;

the membrane defining a volume and further defining at least one orifice in a surface of the membrane, wherein the embolizing device is adapted to reduce a pressure within the volume when reconfigured such that fluid is aspirated through the at least one orifice into the volume.

2. The embolizing device of claim 1 wherein the member is attached to a joint.

3. The embolizing device of claim 2 wherein the device is connected via the joint to a delivery catheter for insertion into the aneurysm.

4. The embolizing device of claim 3 wherein the joint is adapted to release the device from the delivery catheter upon an expansion of the member.

5. The embolizing device of claim 3 wherein the volume defined by the membrane is in fluid communication with a proximal end of the delivery catheter.

6. The embolizing device of claim 3 wherein the device is in electrical communication with a proximal end of the delivery catheter.

7. The embolizing device of claim 2 wherein the joint comprises a detachable mechanical joint.

8. The embolizing device of claim 7 wherein the detachable mechanical joint is selected from the group consisting of hooks, barbs, keyed couplings, and friction-fitted couplings.

9. The embolizing device of claim 2 wherein the joint comprises a detachable electrolytic joint.

10. The embolizing device of claim 9 wherein the electrolytic joint is electrically connected to a voltage source.

11. The embolizing device of claim 1 wherein the member numbers at least two.

12. The embolizing device of claim 1 wherein the member is comprised of a shape memory alloy.

13. The embolizing device of claim 12 wherein the shape memory alloy comprises Ni—Ti alloy.

14. The embolizing device of claim 12 wherein the member is adapted to be compressed into a first configuration and then expand into a second configuration.

15. The embolizing device of claim 14 wherein the second configuration comprises a coil.

16. The embolizing device of claim 14 wherein the first configuration comprises a first diameter and the second configuration comprises a greater second diameter.

17. The embolizing device of claim 14 wherein the first configuration comprises a cross-sectional shape selected from the group consisting of circles, ellipses, stars, rectangles, and squares.

18. The embolizing device of claim 14 wherein the second configuration comprises a shape selected from the group consisting of spheres and disks.

19. The embolizing device of claim 14 wherein the member expands from the first configuration into the second configuration upon application of a stimulus to the member.

20. The embolizing device of claim 19 wherein the stimulus is selected from the group consisting of heat, electrical energy, and RF energy.

21. The embolizing device of claim 1 wherein the membrane is distensible.

22. The embolizing device of claim 1 wherein the membrane is comprised of a biocompatible material.

23. The embolizing device of claim 22 wherein the biocompatible material comprises a material selected from the group consisting of silicone, silicone elastomers, latex, and polyurethane.

24. The embolizing device of claim 22 wherein the biocompatible material comprises a material which polymerizes upon exposure to light.

25. The embolizing device of claim 24 wherein the light comprises ultraviolet light.

26. The embolizing device of claim 1 wherein a distal end of the member is attached within the volume to an interior surface of the membrane.

27. The embolizing device of claim 26 wherein the membrane is disposed over a catheter distal end and is adapted to slide relative to the catheter distal end such that the member is drawn distally into the volume.

28. The embolizing device of claim 27 wherein the membrane is urged to slide by introduction of a fluid into the volume.

29. The embolizing device of claim 28 wherein the fluid comprises saline or water.

30. The embolizing device of claim 28 wherein the fluid has a pressure which is maintained by a reservoir in communication with the volume.

31. The embolizing device of claim 1 wherein the membrane comprises a wall having a thickness of about 0.0005 to about 0.0015 inches.

32. The embolizing device of claim 1 wherein the membrane comprises a wall having a thickness of about 0.001 inches.

33. The embolizing device of claim 1 wherein the member contacts an inner surface of the membrane.

34. The embolizing device of claim 1 wherein the member is integral with the membrane.

35. The embolizing device of claim 1 wherein the orifice has a diameter of about 0.0001 to 0.010 inches.

36. The embolizing device of claim 1 wherein the orifice has a diameter of about 0.005 inches.

37. The embolizing device of claim 1 wherein the membrane further defines a plurality of additional orifices in the surface of the membrane.

38. A method of embolization, comprising:
increasing a volume enclosed by a distensible membrane by stretching an elastomeric material, the distensible membrane defining at least one orifice;
aspirating through the orifice and into the volume a quantity of blood surrounding the distensible membrane; and
coagulating the quantity of blood.

39. The method of claim 38 wherein increasing the volume enclosed by the distensible membrane comprises changing a plurality of resilient members enclosed by the distensible membrane from a first configuration to a second configuration.

40. The method of claim 39 wherein the resilient members are attached to a joint.

41. The method of claim 39 wherein the resilient members comprise a shape memory alloy.

42. The method of claim 41 wherein the shape memory alloy comprises Ni—Ti alloy.

43. The method of claim 39 wherein the second configuration comprises a shape selected from the group consisting of spheres and disks.

44. The method of claim 39 wherein changing the plurality of resilient members comprises applying a stimulus to the resilient members.

45. The method of claim 44 wherein the stimulus is selected from the group consisting of heat, electrical energy, and RF energy.

46. The method of claim 38 wherein the quantity of blood is aspirated through the orifice and into the volume by reducing a pressure within the volume.

47. The method of claim 38 wherein coagulating the quantity of blood comprises allowing the blood to undergo stasis.

48. The method of claim 38 wherein coagulating the quantity of blood comprises applying a stimulus to the quantity of blood.

49. The method of claim 48 wherein the stimulus is selected from the group consisting of chemical factors, mechanical factors, and electrical charges.

50. The method of claim 49 wherein the chemical factors are selected from the group consisting of thrombin, fibrin, and platelet extracts.

51. The method of claim 49 wherein the mechanical factors are selected from the group consisting of fibers and platinum coatings.

52. The method of claim 38 further comprising releasing the distensible membrane from a delivery catheter into an aneurysm.

53. The method of claim 38 wherein increasing the volume enclosed by the distensible membrane comprises inserting at least one resilient member into the volume such that the resilient member changes from a first configuration to a second configuration.

54. The method of claim 53 wherein the second configuration comprises a coil.

55. The method of claim 53 wherein a distal end of the resilient member is attached within the volume to an interior surface of the membrane.

56. The method of claim 55 wherein the resilient member comprises a shape memory alloy.

57. The method of claim 56 wherein the shape memory alloy comprises Ni—Ti alloy.

* * * * *